US00PP35630P2

(12) United States Plant Patent
Meilland

(10) Patent No.: US PP35,630 P2
(45) Date of Patent: Feb. 6, 2024

(54) MINIATURE ROSE PLANT NAMED 'MEIZONBLA'

(50) Latin Name: *Rosa hybrida*
Varietal Denomination: MEIZONBLA

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 58 days.

(21) Appl. No.: 18/086,869

(22) Filed: Dec. 22, 2022

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./123, 116, 125, 126, 118, 119, 121
CPC ... A01H 5/02; A01H 5/00; A01H 6/74; A01H 6/749
See application file for complete search history.

(56) References Cited

U.S. PATENT DOCUMENTS

| | | | | |
|---|---|---|---|---|
| PP9,652 | P | 10/1996 | Meilland | |
| PP16,202 | P2 | 1/2006 | Radler | |
| PP17,481 | P3 * | 3/2007 | Meilland | A01H 5/02 Plt./116 |

OTHER PUBLICATIONS

Mobilian, Star Roses and Plants to showcase new varieties at Cultivate'22, Greenhouse Management 2022, retrieved on Mar. 8, 2023 at https://www.greenhousemag.com/news/star-roses-and-plants-to-showcase-new-varieties-at-cultivate-22/, 14 pp. (Year: 2022).*
Star Roses and Plants for Sunblaze Peach, retrieved on Mar. 8, 2023 at https://www.starrosesandplants.com/plants/sunblaze-peach/, 4 pp. (Year: 2023).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIZONBLA', is disclosed. The new variety forms attractive, semi-double yellow pink colored flowers. Attractive semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEIZONBLA'.

STATEMENT REGARDING PRIOR DISCLOSURES BY THE INVENTOR

The first offer for sale of the new variety was Mar. 4, 2022 in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'MEINEYTA' variety (not patented). The male parent (i.e., the pollen parent) of the new variety was an unnamed seedling (not patented) from the cross between an unnamed seedling (not patented) and the 'RADTKO' variety (U.S. Plant Pat. No. 16,202).

The parentage of the new variety can be summarized as follows:

'MEINEYTA' x (Unnamed Seedling x 'RADTKO')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms yellow pink colored flowers, (b) produces semi-double flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEINEYTA' variety (i.e., seed parent) displays flowers with a more starlike shape, whereas the new variety displays flowers with a more cuplike shape. In addition, the unnamed pollen parent (Unnamed Seedling x 'RADTKO') produces red colored flowers, whereas the new variety produces yellow pink colored flowers. Moreover, the new variety can be readily distinguished from other similar non-parental varieties. For example, the 'MEIFERJAC' variety (U.S. Plant Pat. No. 9,652) produces smaller sized flowers that are orange in color compared to the new variety which produces yellow pink colored flowers. As another example, the 'Meigenpi' variety (U.S. Plant Pat. No. 17,481) produces flowers with 57-70 petals, whereas the new variety produces flowers with 20 petals.

The new variety has been named 'MEIZONBLA'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during July while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a flowering stem.

Element 11—illustrates a specimen of a floral receptacle showing arrangement of the stamens and pistils.

Element 12—illustrates a specimen of a floral receptacle showing arrangement of the pistils (stamens removed).

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during July while budded on their own roots and growing outdoors at Le Cannet des Maures, Var, France.

Botanical classification: *Rosa hybrida* cultivar MEIZONBLA.

Commercial classification: Miniature Rose Plant.

Plant:

*Habit*.—Bushy.

*Height*.—Commonly between 25 cm to 35 cm.

*Width*.—Commonly between 35 cm to 45 cm.

Branches:

*Color*.—Young stems: commonly a color which is a color between near Yellow-Green Group 144A and Green Group 143A. — adult wood: commonly near Green Group 141A suffused with near Green Group 139B.

*Length*.—From the crown to the flower is typically between 20 cm to 25 cm.

*Diameter*.—Approximately 0.4 cm on average.

*Young shoots*.—Anthocyanin coloration: commonly near Greyed-Red Group 178A.

*Thorns*.—Configuration on adult stems: rather upright, elongated, and curved downward on the upper surface and concave on the under surface. — long prickles — quantity: commonly between 5 to 10 thorns per 10 cm long young stem and commonly between 10 to 15 thorns per 10 cm long adult stem. — long prickles — length: typically between 0.4 cm to 0.6 cm on young stems and typically between 0.3 cm to 0.7 cm on adult stems. — long prickles — width: approximately 0.1 cm on average on young stems and approximately 0.2 cm on average on adult stems. — long prickles — base: shape is narrow obovate to short broad on young stems; shape is majority amply obovate and sometimes narrow obovate to short broad on adult stems. — long prickles — color on young stems: commonly near Yellow-Green Group 144A. — long prickles — color on adult stems: commonly near Greyed-Orange Group 164B. — small prickles — quantity: absent.

*Internode*.—Numbers on the entire branch: typically between 5 to 8. — length: approximately 2.0 cm on average.

Foliage:

*General appearance*.—Very dense, darker with a semi-glossy aspect.

*Number of leaflets*.—3, 5, 7; most often 5.

5 *leaflets leaf length*.—Approximately 8.3 cm on average. — width: typically between 5.0 cm and 7.0 cm.

*Terminal leaflet*.—Length: approximately 4.4 cm on average. — width: approximately 2.5 cm on average.

*New foliage*.—Upper surface color: commonly near Green Group 137A. — under surface color: commonly near Green Group 138B. — anthocyanin coloration: absent.

*Adult foliage*.—Upper surface color: commonly near Green Group 139A. — under surface color: commonly near Green Group 139B. — anthocyanin coloration: absent.

Leaflets:

*Shape*.—Top: acuminate. — base: obtuse.

*Glossiness of upper surface*.—Medium.

*Texture*.—Upper and under surfaces are thick.

*Smoothness*.—Upper surface is smooth; under surface is bumpy.

*General appearance*.—Oval.

*Serration*.—Small and single.

*Undulation on the margin*.—Medium.

*Venation*.—Color is commonly near Yellow-Green Group 144B and pattern is imparipinnate.

*Petiole rachis*.—Color of upper surface: commonly near Yellow-Green Group 144B suffused with near Green Group 143A. — color of under surface: commonly near Yellow-Green Group 144B. — texture: upper surface is very few glandular, under surface is smooth (rarely prickly). — rachis of terminal leaflet: length is commonly between 3.0 cm to 4.0 cm and diameter is approximately 0.1 cm on average.

*Petioles*.—Upper surface: no glandular. — under surface: no prickles. — color of upper surface: commonly near Yellow-Green Group 144B suffused with near Green Group 143A. — color of under surface: commonly near Yellow-Green Group 144B. — length: approximately 1.6 cm on average. — diameter: approximately 0.1 cm on average.

*Stipules*.—Length: approximately 0.8 cm on average. — width: typically between 0.2 cm to 0.4 cm. — general appearance: rather broad. — texture: smooth. — color of upper surface: commonly near Yellow-Green Group 144A. — color of under surface: commonly near Yellow-Green Group 144A suffused with near Green Group 143A.

Inflorescence:

*Number of flowers per stem*.—Between 1 and 4 flowers per stem.

*Lastingness of the bloom*.—On the plant: approximately 15 days. — in vase: not tested.

*Bud*.—Shape: conical. — size: small. — length: typically between 2.0 cm to 2.5 cm. — width: approximately 1.5 cm on average. — color as calyx breaks: upper surface: commonly near Yellow Group 7B covered with near Red Group 39B with tiny little spots and areas of near Red Group 51A, basal spot is very little and near Yellow Group 7A. under surface: commonly near Yellow Group 7C covered with near Red Group 39B with tiny little spots and areas of near Red Group 51A on the edge of the petal, basal spot is very little and near Yellow Group 7B.

*Sepals*.—Number commonly 5. — length: approximately 2.1 cm on average. — width: approximately 0.5 cm on average (on median part). — shape: at the top: elongated and narrow. at the base: flat at union with the receptacle. — extensions: 1 very strong, 2 absent or very weak, and 2 weak to medium. — upper surface: texture: tomentous. color: commonly near Yellow-Green Group 144C in the middle covered with near Green Group 143A on the edges and covered with many hairs near Green- White Group 157B. — under surface: texture: glandular. color: commonly near Yellow-Green Group 144C in the middle covered with near Green Group 143A on the edges.

*Receptacle*.—Color: commonly near Green Group 143B suffused with near Green Group 143A. — length: approximately 0.7 cm on average. — width: approximately 0.7 cm on average (on median part). — surface: smooth. — shape: pitcher shaped.

*Peduncle*.—Length: typically between 3.0 cm to 3.5 cm. — width: approximately 0.1 cm on average. — surface: smooth. — color: commonly near Green Group 143B suffused with near Green Group 143A.

*Flower*.—Diameter when open: approximately 5.0 cm on average. — depth of the flower: approximately 2.5 cm on average. — shape: flat cup shaped. — shape when viewed from above: irregular rounded. shape of the upper part of the flower profile: flattened convex. — shape of the lower part of the flower profile: convex. — type: semi-double. — number of petals under normal conditions: typically 20 petals. — petals: shape: obovate (acute at the base and rounded at the top). texture: dry. length: approximately 2.6 cm on average. width: approximately 2.0 cm on average. — undulation of the petal: weak. — reflexing of the petal: very weak. — petal incision: very weak. — petal arrangement: imbricated with few, small and creased petaloids. — petal drop: petals drop off cleanly before drying. — fragrance: none. — discoloration of the flower: slightly fainting. — color when opening: basal spot on the upper surface: commonly near Yellow Group 8B; size is small to medium. upper surface: commonly near Yellow Group 8B covered with near Red-Purple Group 62A with tiny little spots and areas near Red-Purple Group 63B; more or less margined with near Red-Purple Group 62A and Red-Purple Group 63B. basal spot on the under surface: commonly near Yellow Group 8C. under surface: commonly near Yellow Group 8C covered with tiny little spots of near Red-Purple Group 62A; more or less margined with near Red-Purple Group 62A and Red-Purple Group 63B. — color of the open flower: basal spot on the upper surface: commonly near Yellow Group 8C; size is small to medium. upper surface of the flower: commonly near Yellow Group 8C covered with near Red-Purple Group 62A with large areas and spots of near Red-Purple Group 63B; more or less margined with near Red-Purple Group 62A and Red-Purple Group 63B. basal spot on the under surface: commonly near Yellow Group 8D. under surface of the flower: commonly near Yellow Group 8D with tiny little spots of near Red-Purple Group 62A and 63B; more or less margined with near Red-Purple Group 62A and Red-Purple Group 63B.

— color of the flower when fading: same color as the open flower. — anthers: number is 120 on average, length is approximately 0.1 cm on average, width is approximately 0.1 cm on average, coloration is commonly near Yellow Group 8A, and arrangement is regular around styles. — filaments: length is approximately 0.5 cm on average and coloration is commonly near Orange Group 24A. — styles: length is approximately 0.4 cm on average, coloration is commonly near Green-White Group 157A with various tints of near Red-Purple Group 58B on some of them, and number is approximately 45 on average. — stigmas: length is approximately 0.1 cm on average and coloration is commonly near Yellow Group 5C. — pollen: color is commonly near a color between Orange Group 24A and Orange Group 25A and amount is abundant. — hips: not observed to date.

Development:

*Vegetation*.—Very strong.

*Blooming*.—Early in the season, normal and recurrent, typically from May to October in France.

*USDA hardiness zone*.—Zone 5 to 11.

*Tolerance to disease*.—Very good, and particularly against rust (*Phragmidium sp*).

The new 'MEIZONBLA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIZONBLA' characterized by the following combination of characteristics:

(a) forms yellow pink colored flowers, (b) produces semi-double flowers, and (c) exhibits a bushy growth habit;

substantially as herein shown and described.

* * * * *

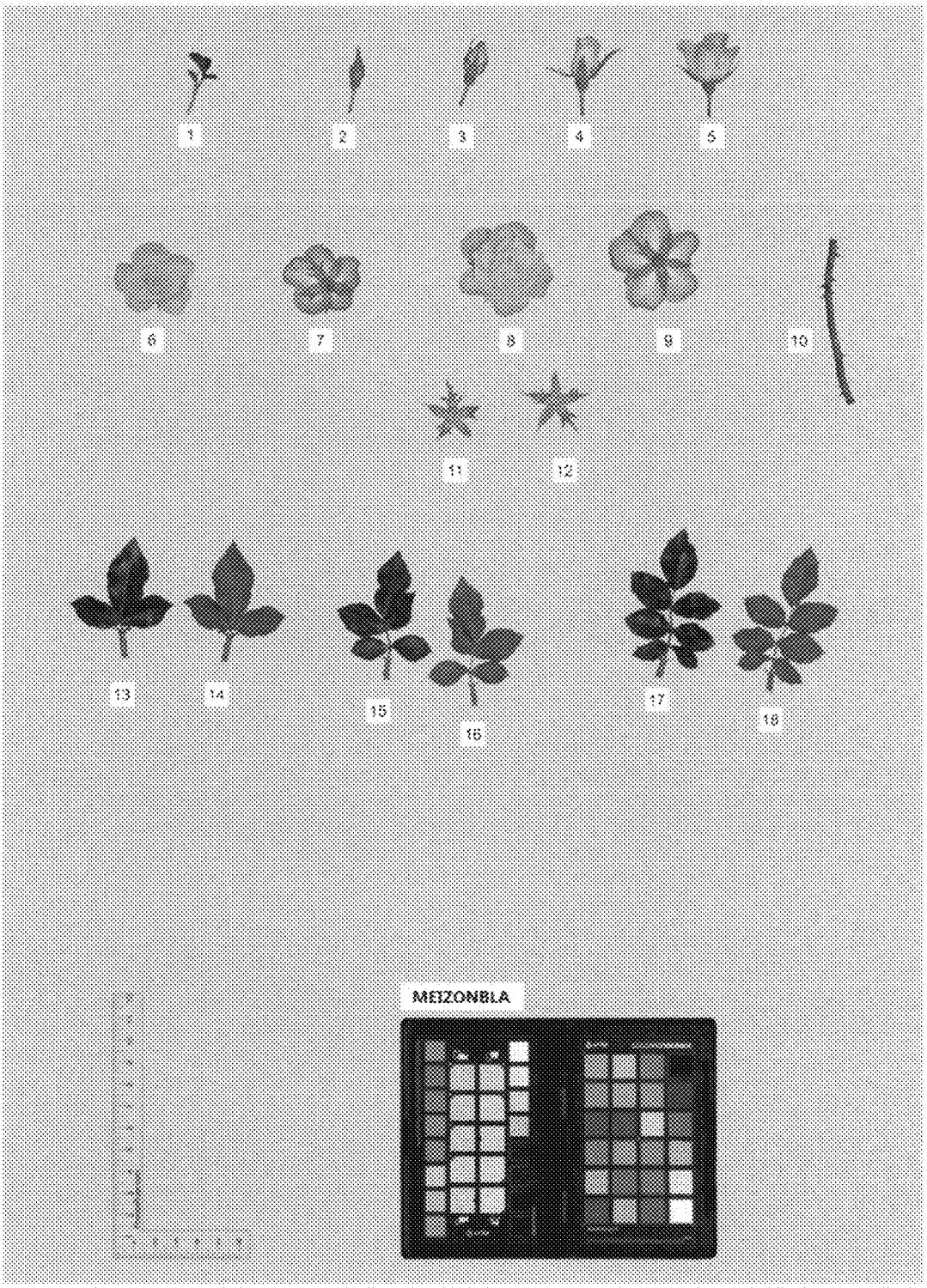
1
2
3
4
5
6
7
8
9
10
11
12
13
14
15
16
17
18
MEIZONBLA